(12) United States Patent
Sachdeva et al.

(10) Patent No.: US 11,806,930 B1
(45) Date of Patent: Nov. 7, 2023

(54) ADAPTOR FOR ADDITIVE MANUFACTURING DEVICE THAT IMPROVES PRINTING EFFICIENCY BY REDUCING RESIN USAGE

(71) Applicant: Florida A&M University, Talahassee, FL (US)

(72) Inventors: Mandip Sachdeva, Tallahassee, FL (US); Arvind Bagde, Tallahassee, FL (US); Keb Mosley-Kellum, Tallahassee, FL (US); Satyanarayan Dev, Tallahassee, FL (US); Thanh Dinh, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 14 days.

(21) Appl. No.: 17/444,444

(22) Filed: Aug. 4, 2021

Related U.S. Application Data

(60) Provisional application No. 63/060,946, filed on Aug. 4, 2020.

(51) Int. Cl.
*B29C 64/255* (2017.01)
*B29C 64/129* (2017.01)
*B33Y 30/00* (2015.01)
*B33Y 10/00* (2015.01)

(52) U.S. Cl.
CPC .......... *B29C 64/255* (2017.08); *B29C 64/129* (2017.08); *B33Y 10/00* (2014.12); *B33Y 30/00* (2014.12)

(58) Field of Classification Search
None
See application file for complete search history.

(56) References Cited

U.S. PATENT DOCUMENTS

| | | | |
|---|---|---|---|
| 2018/0169940 A1* | 6/2018 | Dunne | B33Y 30/00 |
| 2020/0094469 A1* | 3/2020 | Holt | B29C 64/232 |

* cited by examiner

*Primary Examiner* — Yung-Sheng M Tsui
(74) *Attorney, Agent, or Firm* — Owen G. Behrens; Paul Murty; Smith & Hopen, P.A.

(57) ABSTRACT

A multi-component adaptor assembly including a resin reservoir adaptor disposed on a printing surface of a preexisting additive manufacturing device, and including a build platform adaptor secured to a translatable arm of the preexisting additive manufacturing device. The resin reservoir adaptor is used to modify an existing resin reservoir by creating one or more smaller reservoirs within the larger housing, thereby reducing an amount of resin stored within the device to reduce resin waste. Moreover, the rotating and/or sliding build platform adaptor is designed to selectively contact one or more of the reservoirs of the resin reservoir adaptor, thereby selectively printing components of an additive manufactured process. The multi-component adaptor assembly allows for additive manufacturing projects using less resin with fewer waste products; simultaneous printing of identical structures; and the selective printing of different components of a structure during a single printing cycle.

10 Claims, 14 Drawing Sheets

ADAPTOR FOR ADDITIVE MANUFACTURING DEVICE THAT IMPROVES PRINTING EFFICIENCY BY REDUCING RESIN USAGE

CROSS-REFERENCE TO RELATED APPLICATIONS

This nonprovisional application is a continuation of and claims priority to provisional application No. 63/060,946, entitled "3D printing adaptors for the manufacturing of microneedles using a biocompatible resin," filed on Aug. 4, 2020, by the same inventors.

BACKGROUND OF THE INVENTION

1. Field of the Invention

This invention relates, generally, to additive manufacturing devices. More specifically, it relates to a multi-reservoir adaptor and corresponding print platform adaptor that can be retrofit into existing additive manufacturing devices, or can be manufactured together with a new additive manufacturing device. The multi-reservoir adaptor and corresponding print platform adaptor contributes to an improvement in printing efficiency by reducing resin usage during an additive manufacturing process.

2. Brief Description of the Prior Art

Resin-based additive manufacturing devices, such as photopolymerization-based devices that cure liquid resin into a solid printed structure, have seen increasing usage over the past few decades. Typical additive manufacturing devices include a resin material therein to be used in printing projects; however, the standard resins tend to cure into rigid structures that are not easily dissolvable in water or other fluids. As such, the standard resins are not universally useful for printing projects, particularly those relating to dissolvable printed materials.

In addition, standard additive manufacturing devices include a build platform and a singular resin reservoir, such that the build platform is used in combination with the resin reservoir to manufacture a given structure. During a printing process, the build platform interacts with the resin reservoir to obtain an amount of the resin, depending on the printed component of the device. In a typical device, the resin reservoir measures approximately 15 cm×15 cm, holding approximately 125 mL of liquid resin material therein. Over time, the resin may denature or otherwise become unusable in a printing process; accordingly, there is a great deal of inefficiency by way of wasted resin material.

Furthermore, due to the singular resin reservoir, current additive manufacturing machines are limited in terms of utilizing various resin materials within the same print cycle. As such, the control of an end product-specific multi-layered deposition or concentration gradients in an additive manufactured final product is also limited, since the build platform can only utilize a single type of resin within the singular resin reservoir.

Accordingly, what is needed is a multi-reservoir adaptor, and corresponding print platform adaptor, that is designed to reduce an amount of resin stored within a resin reservoir of an additive manufacturing device, thereby reducing an inefficiency of the device by reducing resin waste. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a multi-component adaptor assembly for use in combination with an additive manufacturing device is now met by a new, useful, and nonobvious invention.

The novel multi-component adaptor assembly includes a resin reservoir adaptor disposed on a printing surface of an additive manufacturing device. The resin reservoir adaptor includes a reservoir having an associated area and an associated volume less than an associated area and an associated volume of the printing surface. The reservoir includes a plurality of interior walls including a set of opposing longitudinal walls each having substantially equal dimensions, and a set of opposing lateral walls each having substantially equal dimensions. A cavity is defined by the plurality of interior walls, such that the cavity is defined by a width equal to a distance between the opposing longitudinal walls, and such that the cavity is defined by a length equal to a distance between the opposing lateral walls. In an embodiment, the distance between the opposing longitudinal walls is 3 cm and the distance between the opposing lateral walls is 6 cm, such that the cavity is configured to receive a volume of the resin equaling 10 mL.

The multi-component adaptor assembly includes a build platform adaptor including a connector disposed above a printing platform. The connector configured to be received by a translatable printing arm of the additive manufacturing device, such that the printing platform of the build platform adaptor is disposed above the resin reservoir adaptor. The printing platform includes an associated length that is less than the length defining the cavity of the resin reservoir adaptor and including an associated width that is less than the width defining the cavity of the resin reservoir adaptor.

In an embodiment, the length of the printing platform is 2 cm and the width of the printing platform is 2 cm, such that the printing platform is receivable within the resin reservoir adaptor via the cavity.

In use, the printing platform is configured to be received within the resin reservoir adaptor via insertion into the cavity. The resin reservoir adaptor is configured to store an amount of resin therein within the cavity. The printing platform is configured to print an additive manufactured structure via at least a portion of the amount of resin stored within the cavity, such that a reduced amount of resin is used to print the additive manufactured structure.

In an embodiment, the resin reservoir adaptor includes a transparent bottom surface wall that defines the cavity together with the plurality of interior walls. The transparent bottom surface wall is configured to allow ultraviolet light to pass therethrough to cure the additive manufactured structure.

An embodiment of the resin reservoir adaptor includes a plurality of interconnected reservoirs having equal area and volume. The plurality of interconnected reservoirs include a cumulative area and a cumulative volume that is less than the associated area and the associated volume of the printing surface. In an embodiment, each of the plurality of interconnected reservoirs includes an identical resin, such that a plurality of identical additive manufactured structures can be printed during a single printing cycle. In another embodiment, at least one of the plurality of interconnected reservoirs includes a first resin, and at least another of the plurality of interconnected reservoirs includes a second resin, such that the additive manufactured structure includes a component made from the first resin and a component made from the second resin.

An embodiment of the build platform adaptor includes a plurality of printing platforms, with each of the plurality of printing platforms having equal area and volume. Each of the plurality of printing platforms is simultaneously receivable within the plurality of interconnected reservoirs. In an embodiment, the build platform adaptor includes a translation motor assembly secured at a first end to the connector of the build platform adaptor and secured at an opposing second end to a central point of the plurality of printing platforms, such that the translation motor assembly is configured to rotate the plurality of printing platforms about the central point.

The novel method of printing an additive manufactured structure includes a step of disposing a resin reservoir adaptor on a printing surface of an additive manufacturing machine. A build platform adaptor is secured to a translatable arm of the additive manufacturing machine via a connector of the build platform adaptor. The method includes a step of filling a cavity defined by the resin reservoir adaptor with an amount of a resin. The build platform adaptor is lowered via the translatable arm of the additive manufacturing machine. The printing platform is received within the resin reservoir adaptor via the cavity. The method includes a step of contacting at least a portion of the amount of the resin with the printing platform. An additive manufactured structure is printed with the at least the portion of the amount of the resin via the printing platform.

In an embodiment, the method includes a step of passing ultraviolet light from the printing surface of the additive manufacturing machine through the resin reservoir adaptor to cure the additive manufactured structure. In an embodiment, the resin reservoir adaptor includes a transparent bottom surface wall to allow the ultraviolet let to pass therethrough.

In an embodiment, the resin reservoir adaptor includes a plurality of interconnected reservoirs having equal area and volume, such that the plurality of interconnected reservoirs having a cumulative area and a cumulative volume that is less than the associated area and the associated volume of the printing surface. In an embodiment, the method includes a step of filling each of the plurality of interconnected reservoirs with an amount of an identical resin. In another embodiment, the method includes the steps of filling at least one of the plurality of interconnected reservoirs with a first resin, and filling at least another of the plurality of interconnected reservoirs includes a second resin, such that the additive manufactured structure includes a component made from the first resin and a component made from the second resin.

In an embodiment, the build platform adaptor includes a plurality of printing platforms, with each of the plurality of printing platforms having equal area and volume. In an embodiment, the step of receiving the printing platform within the resin reservoir adaptor includes simultaneously receiving each of the plurality of printing platforms within an associated one of the plurality of interconnected reservoirs. The plurality of printing platforms can be linearly translated while received within the plurality of interconnected reservoirs. In addition, an embodiment of the method includes the steps of raising the plurality of printing platforms via the translatable arm of the additive manufacturing machine, rotating the plurality of printing platforms 90° about the connector, and lowering the plurality of printing platforms to be simultaneously received within each of the plurality of interconnected reservoirs.

An object of the invention is to improve the efficiency of an additive manufacturing device by reducing an amount of resin stored within the device, thereby reducing waste resin during a printing process. Another object of the invention is to provide for the simultaneous manufacturing of identical components to increase a speed of creating additive manufactured structures. Another object of the invention is to provide for the selective printing of different components of a structure during a single printing cycle by providing different resins that are simultaneously used by different printing platforms during the cycle.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a multi-component adaptor assembly designed for use in combination with additive manufacturing devices, such as those employing stereolithography apparatus (SLA) processes, digital light process (DLP), and fused deposition modeling (FDM). The multi-component adaptor assembly includes a resin reservoir adaptor that is used to modify an existing resin reservoir by creating one or more smaller reservoirs within the larger housing, thereby reducing an amount of resin stored within the device to reduce resin waste. In addition, a plurality of smaller reservoirs can be linked together to form a multi-reservoir adaptor that provides for the use of different resins during a printing project. Moreover, the multi-component adaptor assembly includes a rotating and/or sliding build platform adaptor that is designed to selectively contact one or more of the reservoirs of the resin reservoir adaptor, thereby selectively printing components of an additive manufactured process. The multi-component adaptor assembly will be described in greater detail herein below.

Figure 1:
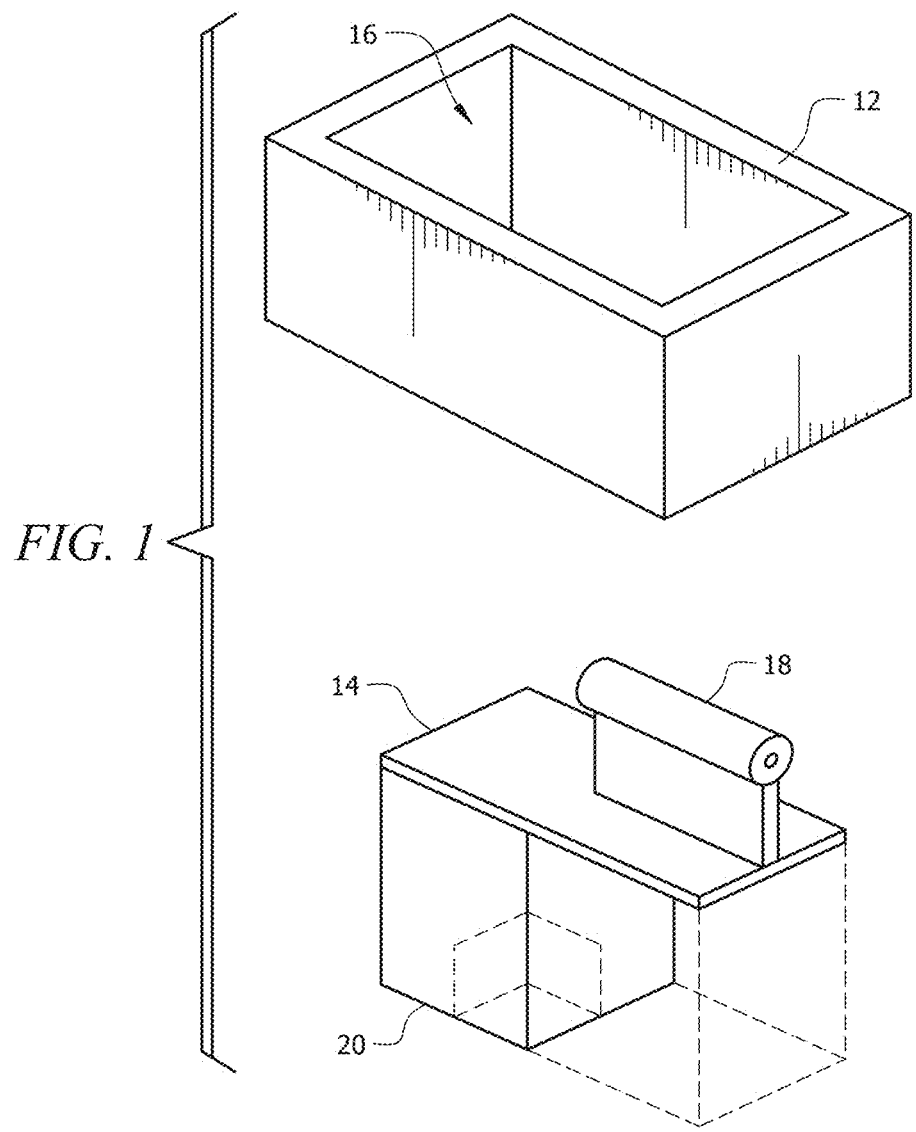
FIG. 1 is a perspective view of a multi-component adaptor assembly including a resin reservoir adaptor and a build platform adaptor, in accordance with an embodiment of the present invention.
Figure 2:
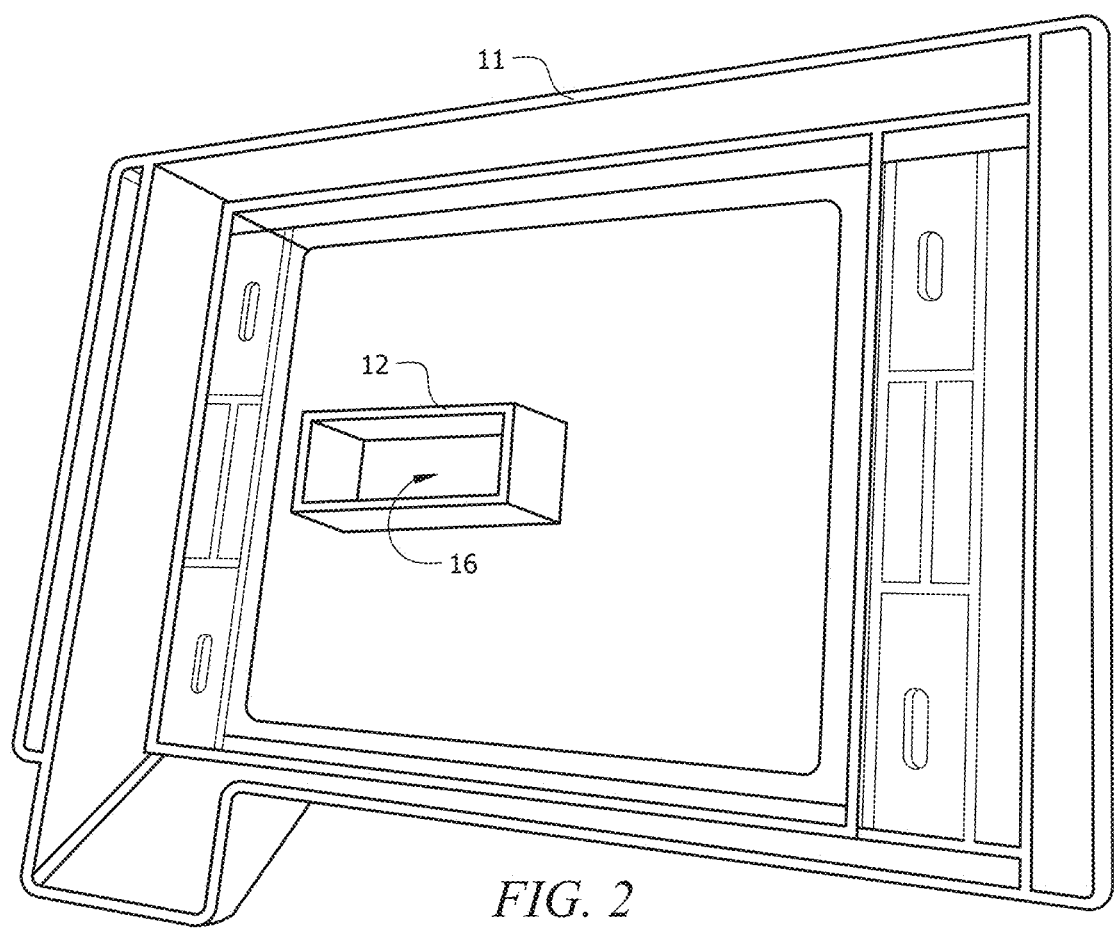
FIG. 2 is a perspective view of the resin reservoir adaptor of FIG. 1 disposed on a preexisting additive manufacturing printing reservoir, in accordance with an embodiment of the present invention.
Figure 3:
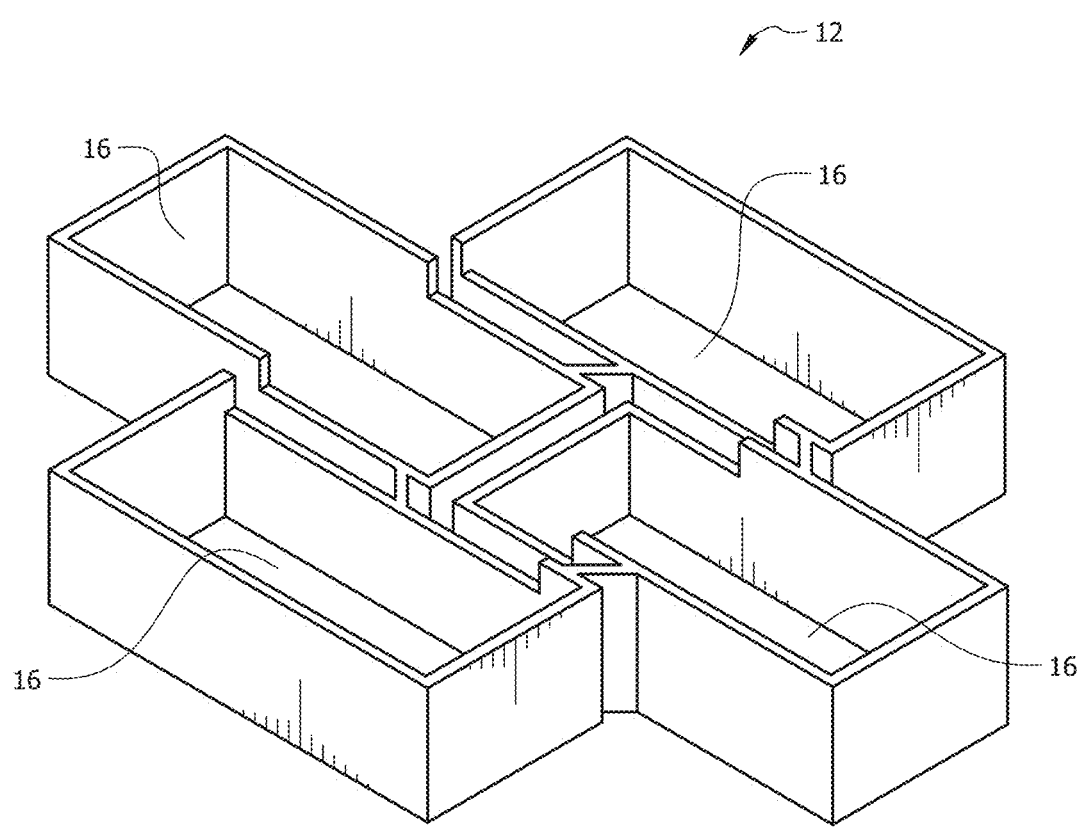
FIG. 3 is a perspective view of a plurality of reservoirs of the resin reservoir adaptor, in accordance with an embodiment of the present invention.

As shown in FIG. 1, the multi-component adaptor assembly includes resin reservoir adaptor 12 (an embodiment of resin reservoir adaptor 12 including a single resin reservoir is shown in FIG. 1; an embodiment of resin reservoir adaptor 12 including a plurality of resin reservoirs is shown in FIG. 3 and is described in greater detail below). Turning to FIG. 2, an embodiment of resin reservoir adaptor 12 including a singular resin reservoir is disposed on a printing surface of preexisting reservoir 11, which is a component of an additive manufacturing device. As such, resin reservoir adaptor 12 creates a separate housing within preexisting reservoir 11, such that different resin materials can be stored in each of resin reservoir adaptor 12 and preexisting reservoir 11. Moreover, embodiments of resin reservoir adaptor 12 are constructed having a transparent bottom surface that is secured to preexisting reservoir 11, or formed without a bottom surface, to allow for the passing of an ultraviolet (UV) light therethrough to aid in a curing process for the resin.

In addition, turning to FIG. 3, an embodiment of resin reservoir adaptor 12 including a plurality of resin reservoirs is shown in greater detail. Each resin reservoir of resin reservoir adaptor 12 includes cavity 16 that is defined by a plurality of interior walls of the reservoir; each cavity 16 is designed to receive an amount of resin disposed therein for use during an additive manufacturing project. The plurality of interior walls include opposing longitudinal walls of substantially equal size, and opposing lateral walls of substantially equal size. The distance between the opposing longitudinal walls defines a width of cavity 16, and the distance between the opposing lateral walls defines a length of cavity 16. In an embodiment, the distance between the opposing longitudinal walls defining cavity 16 is approximately 3 cm, and the distance between the opposing lateral walls defining cavity 16 is approximately 6 cm; however, it should be appreciated that the area defining cavity 16 can be larger or smaller depending on the requirements of the additive manufacturing device.

As noted above, each cavity 16 is designed to receive an amount of resin or other fluid therein. The particular fluid to use within each individual cavity 16 is dependent on the desired result of the additive manufacturing process. In an embodiment, the same fluid is disposed within each individual cavity 16 to facilitate the simultaneous printing of several additive manufactured components having the same structure material. By using the same fluid within each cavity 16, the additive manufacturing device benefits from an increase in printing efficiency, since multiple components can be printed during each printing cycle. In addition, the variance between the components decreases due to the use of the same material during the same printing cycle, resulting in largely identical components.

In another embodiment, one or more different fluids may be disposed within each cavity 16. Accordingly, the additive manufacturing device is capable of selectively generating components with different properties, such as different resin materials, varying drug concentrations, multi-layered poly-drug combinations, washing fluids, and similar fluids that may be used during an additive manufacturing process. As such, the additive manufacturing device is capable of simultaneously printing different components during a single print cycle, while avoiding cross-contamination between cavities 16.

Referring again to FIG. 1, the multi-component adaptor assembly also includes build platform adaptor 14 which includes connector 18 disposed above printing platform 22, such that connector 18 is received within a preexisting additive manufacturing device (shown in greater detail in FIG. 6 and described in the sections below). Build platform adaptor 14 is sized and shaped such that a length and a width of printing platform 22 is smaller than an associated length and width of each cavity 16 of resin reservoir adaptor 12, such that printing platform 22 is insertable into and removable from cavity 16 during a printing process, during which printing platform 22 contacts an amount of resin stored within resin reservoir adaptor 12 to manufacture a given component of an additive manufacturing project. For example, in an embodiment, printing platform 22 includes a length of approximately 2 cm and a width of approximately 2 cm, such that printing platform 22 is insertable within cavity 16; however, it should be appreciated that printing platform 22 can include varying lengths and widths, so long as the length of printing surface 22 is less than the distance separating the lateral walls defining cavity 16, and so long as the width of printing platform 22 is less than the distance separating the longitudinal walls defining cavity 16.

Figure 4A:
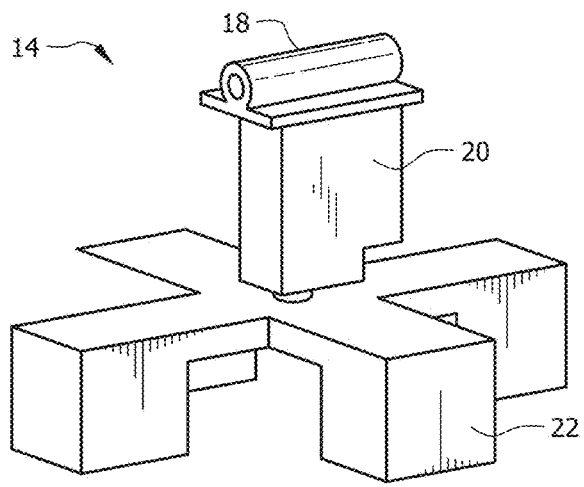
FIG. 4A is a perspective view of a build platform adaptor including a plurality of printing platforms, in accordance with an embodiment of the present invention.
Figure 4B:
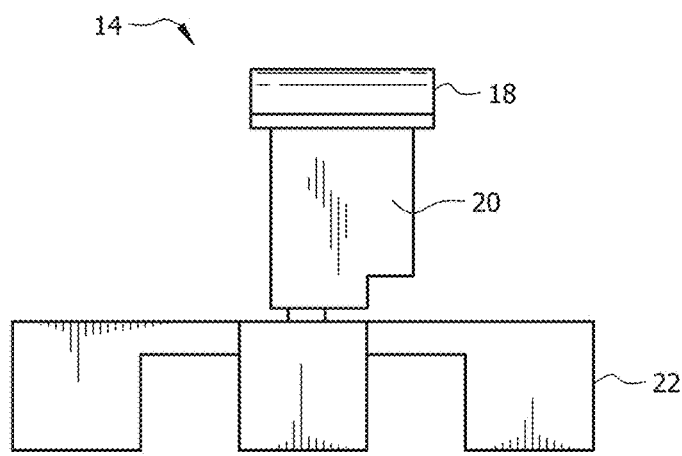
FIG. 4B is a side elevation view of the build platform adaptor of FIG. 4A.
Figure 4C:
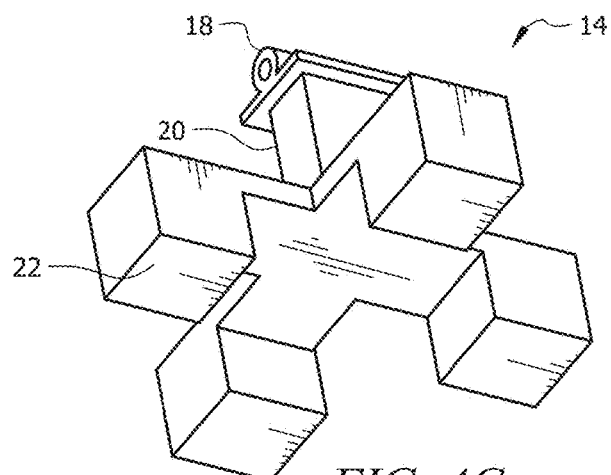
FIG. 4C is a bottom perspective view of the build platform adaptor of FIG. 4A.

As shown in FIGS. 4A-4C, an embodiment of build platform adaptor 14 includes a plurality of printing platforms 22 that are attached at a central point to connector 18 via translation assembly 20, such as a servo motor or other translatable mechanical component. The attachment of plurality of printing platforms 22 to translation assembly 20 is such that the plurality of printing platforms 22 are spaced apart from translation assembly 20, residing within a platform plane, such that translation assembly 20 rotates the plurality of printing platforms 22 thereabout within the platform plane. Translation assembly 20 is in communication with a controlling device. The controlling device includes a mobile device, a wireless remote, a handheld electronic device, a computing nodule, a microcontroller, and any other controlling devices known to a person of ordinary skill in the art. Translation assembly 20 is configured to provide several degrees of movement to printing platforms 22—including roll, yaw, and vertical translation, as will be described in greater detail below.

Figure 5A:
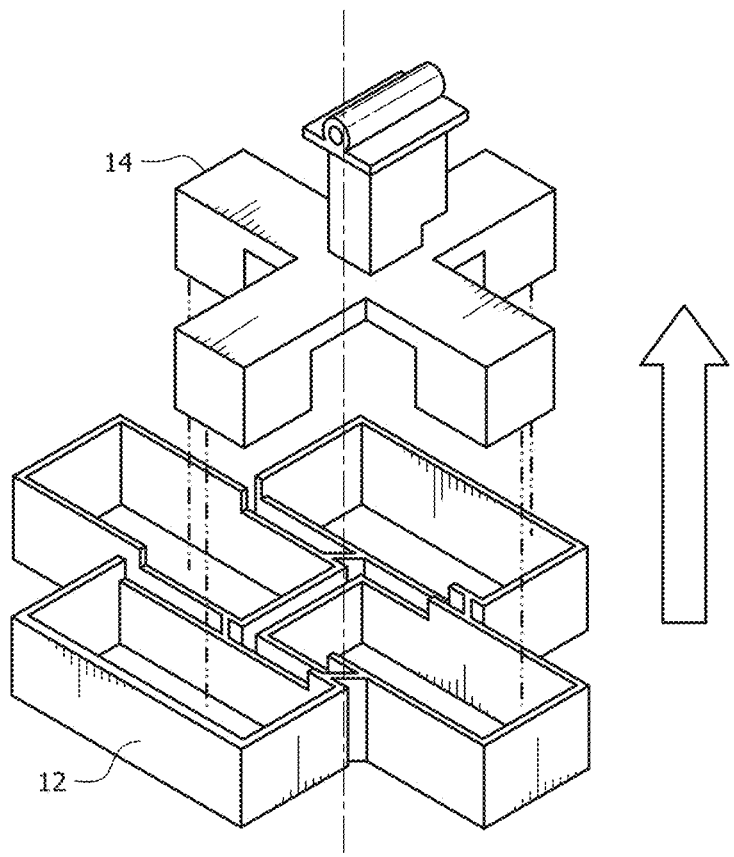
FIG. 5A is a perspective view of a multi-component adaptor assembly including a resin reservoir adaptor having a plurality of reservoirs and a build platform adaptor having a plurality of printing platforms, with the multi-component adaptor assembly shown in a pre-printing configuration, in accordance with an embodiment of the present invention.
Figure 5B:
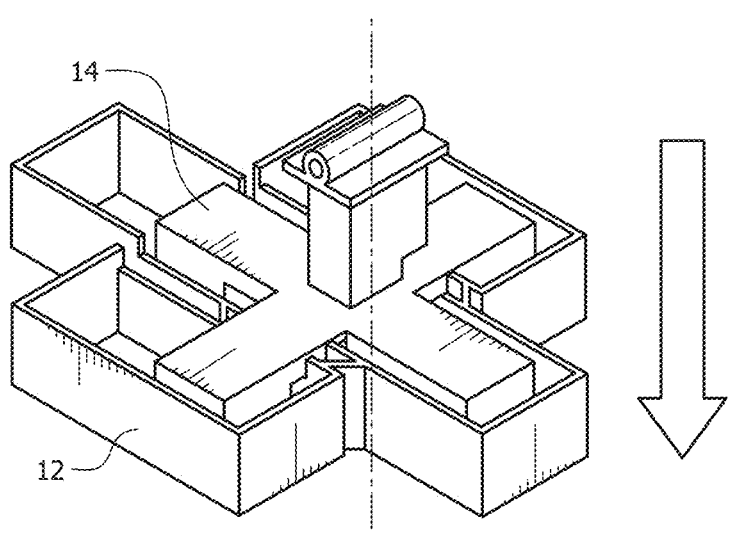
FIG. 5B is a perspective view of the multi-component adaptor assembly of FIG. 5A shown in an initial printing configuration.

Turning to FIGS. 5A-5D, an embodiment of the multi-component adaptor assembly is shown in detail, in which resin reservoir adaptor 12 includes a plurality of reservoirs that are interconnected with one another. Build platform adaptor 14 includes a plurality of printing platforms 22, such as the embodiment described above and shown in FIGS. 4A-4C. Particularly as shown in FIG. 5A, build platform adaptor 14 is disposed at a distance above resin reservoir adaptor 12 in an initial pre-printing configuration. As shown in FIG. 5B, as build platform adaptor 14 receives an instruction to contact one or more of the plurality of reservoirs of resin reservoir adaptor 12, built platform adaptor 14 translates in a direction toward resin reservoir adaptor 12, such that one or more of the plurality of printing platforms 22 resides within one of the plurality of reservoirs of resin reservoir adaptor 12. For example, as shown in FIG. 5B, each of the plurality of printing platforms 22 resides within an associated one of the plurality of reservoirs of resin reservoir adaptor 12. Accordingly, one or more of the plurality of printing platforms 22 is configured to contact an amount of resin disposed within resin reservoir adaptor 12.

Figure 5C:
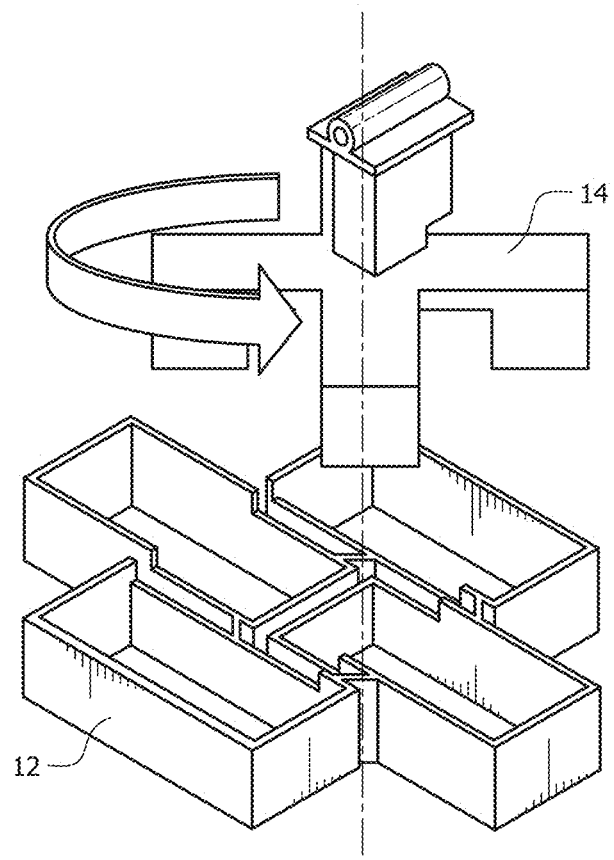
FIG. 5C is a perspective view of the multi-component adaptor assembly of FIG. 5A shown is a rotating configuration.
Figure 5D:
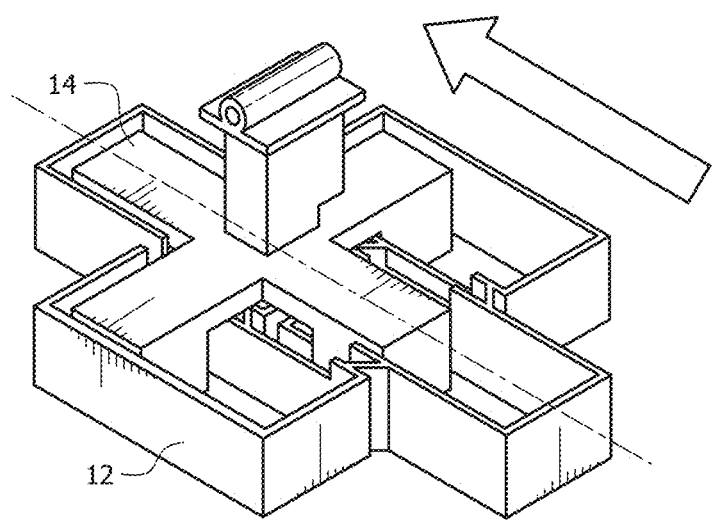
FIG. 5D is a perspective view of the multi-component adaptor assembly of FIG. 5A shown in a second printing configuration.

Moreover, as shown in particular in FIGS. 5C-5D, build platform adaptor 14 is configured to rotate with respect to connector 18, such that connector 18 remains securely connected to an additive manufacturing device without rotation, while the plurality of printing platforms 22 rotate about translation assembly 20. As such, different printing platforms 22 can contact resin or another fluid disposed within resin reservoir adaptor 12 by the rotation of build platform adaptor 14. In addition, as shown in particular in FIG. 5D, an embodiment of build platform adaptor 14 is linearly translatable with respect to resin reservoir adaptor 12 when the adaptors 12, 14 reside within the same plane. As such, the plurality of printing platforms 22 can contact a predetermined amount of resin or other fluid within resin reservoir adaptor 12 by slidably, linearly translating within the cavities 16 of resin reservoir adaptor 12, thereby reducing the volume of resin required for each printing cycle.

Figure 6:
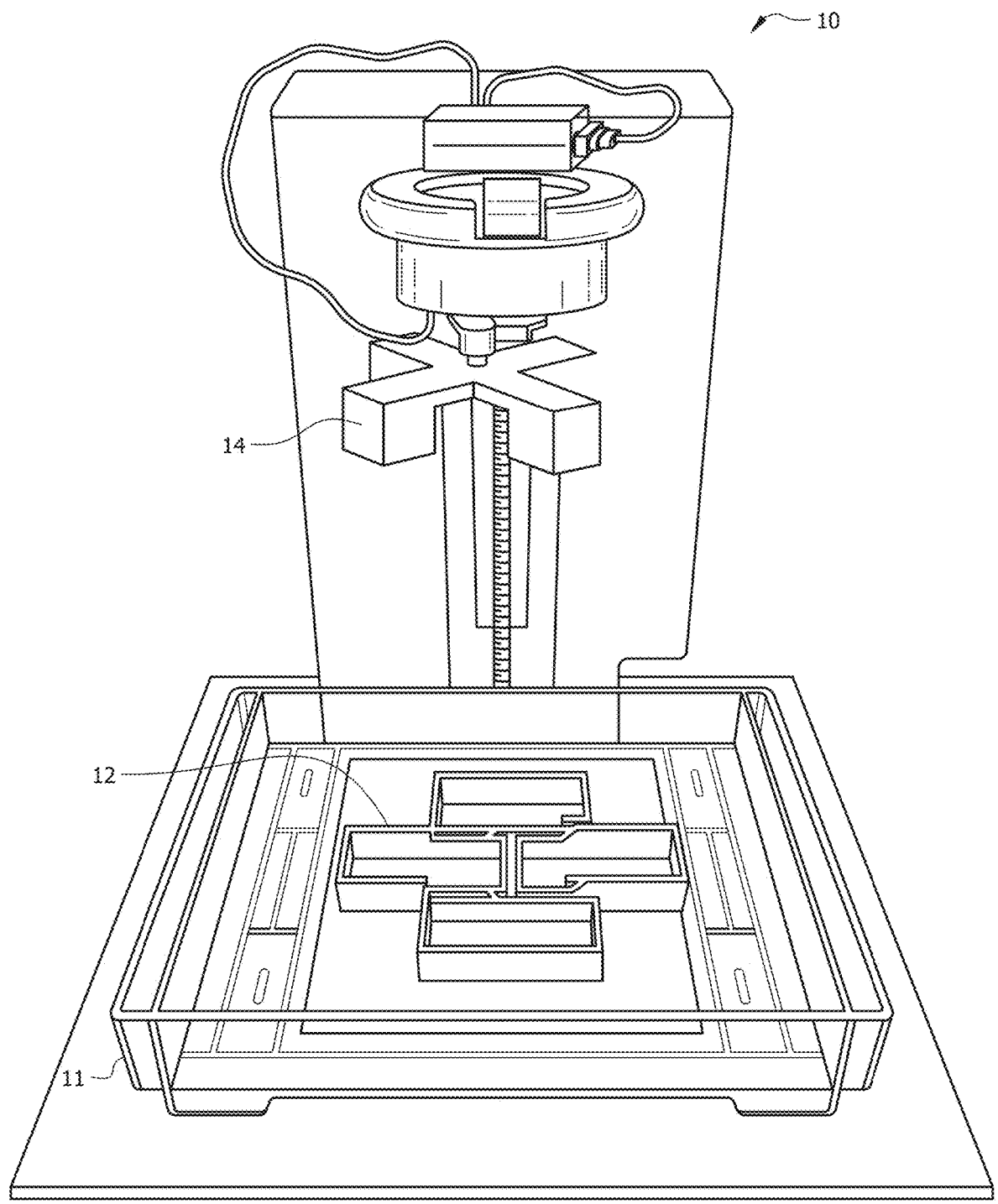
FIG. 6 is a perspective view of an additive manufacturing device including the multi-component adaptor assembly installed thereon, in accordance with an embodiment of the present invention.

Turning now to FIG. 6, an embodiment of a modified additive manufacturing device 10 is depicted, showing an installation of build platform adaptor 14 via connector 18, and showing an installation of resin reservoir adaptor 12 within preexisting reservoir 11. As shown in FIG. 6, rather than relying on a greater volume of resin or other fluid disposed within preexisting reservoir 11, resin reservoir adaptor 12 creates separate housings within preexisting reservoir 11 for resin or other fluids disposed therein for use during a printing project performed by additive manufacturing device 10, as described in detail above.

Figure 7:
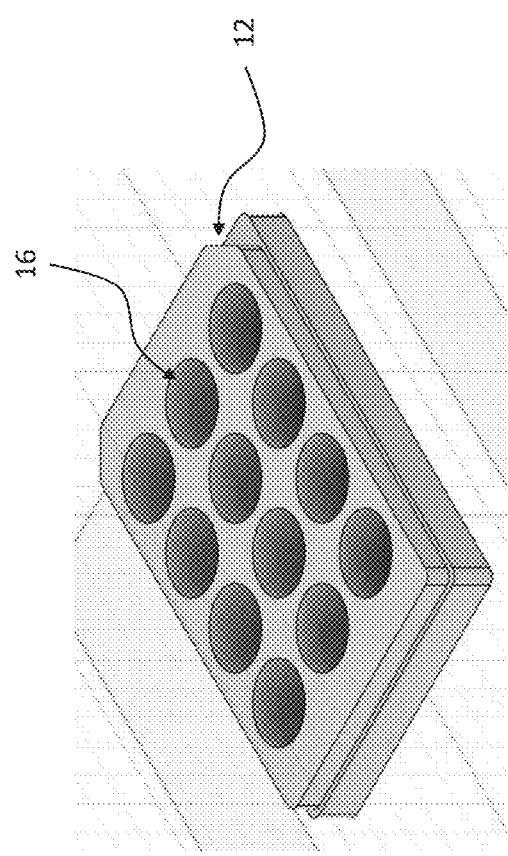
FIG. 7 is a perspective view of a resin reservoir adaptor having a plurality of reservoirs of a multi-component adaptor assembly, in accordance with an embodiment of the present invention.
Figure 8C:
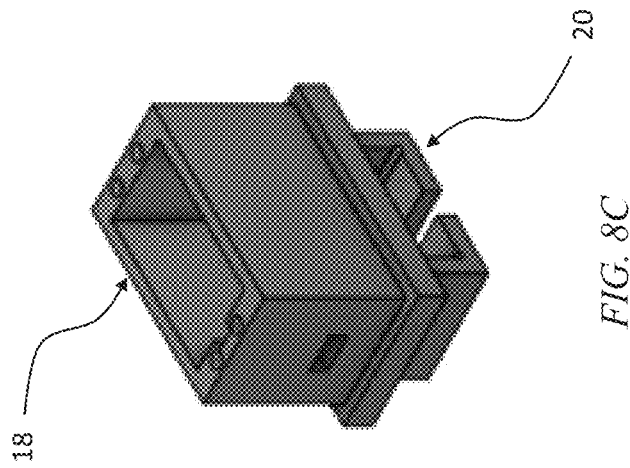
FIG. 8C is a perspective view of a connector and a translation assembly of the build platform adaptor of the multi-component adaptor assembly of FIGS. 8A-8B.
Figure 8B:
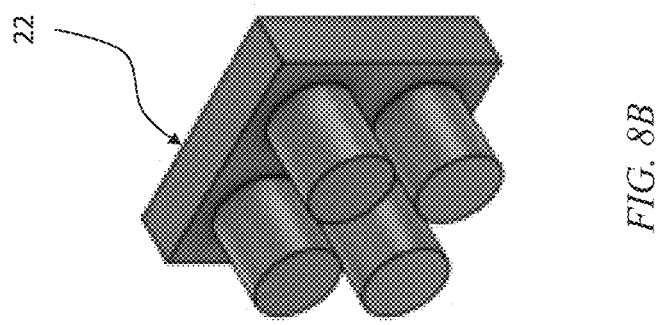
FIG. 8B is a front perspective view of the plurality of printing platforms of FIG. 8A.
Figure 8A:
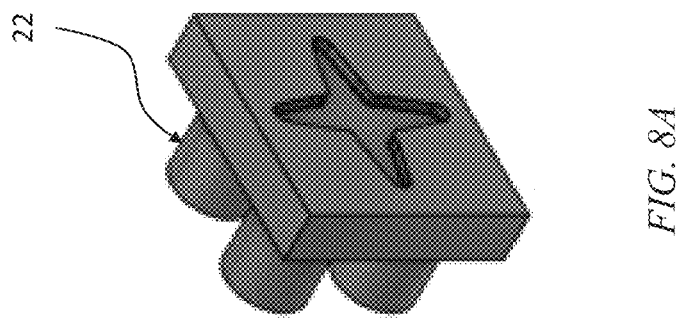
FIG. 8A is a rear perspective view of a portion of a plurality of printing platforms of a build platform adaptor that forms a part of a multi-component adaptor assembly, in accordance with an embodiment of the present invention.
Figure 8D:
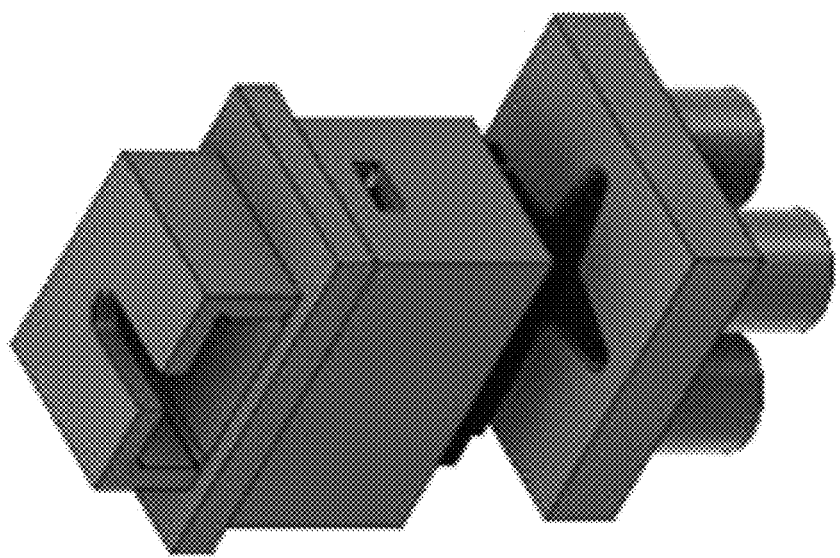
FIG. 8D is a perspective view of an assembled build platform adaptor including the components as shown in FIGS. 8A-8C.
Figure 8D:
Figure 9:
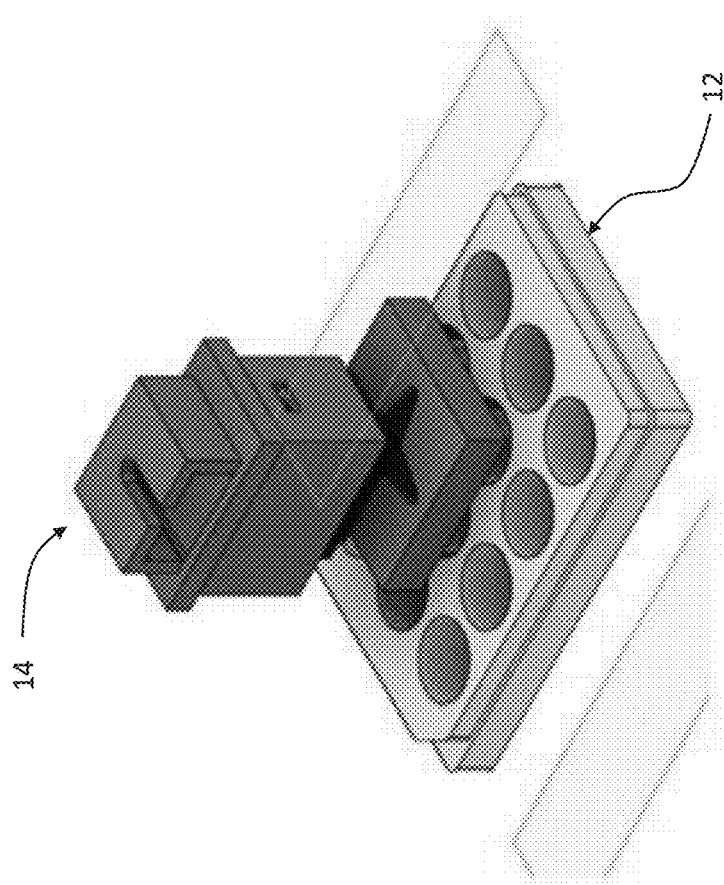
FIG. 9 is a perspective view of the multi-component adaptor assembly of FIGS. 7-8D, in accordance with an embodiment of the present invention.
Figure 10C:
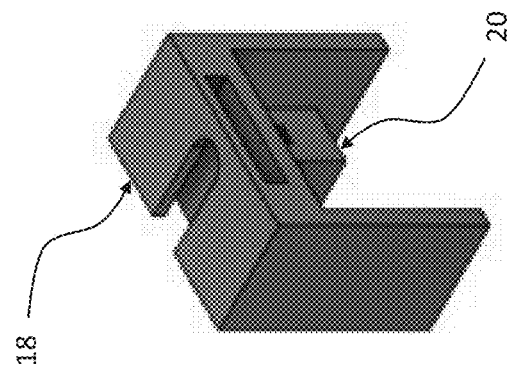
FIG. 10C is a perspective view of a connector and a translation assembly of the build platform adaptor of the multi-component adaptor assembly of FIGS. 10A-10B.
Figure 10B:
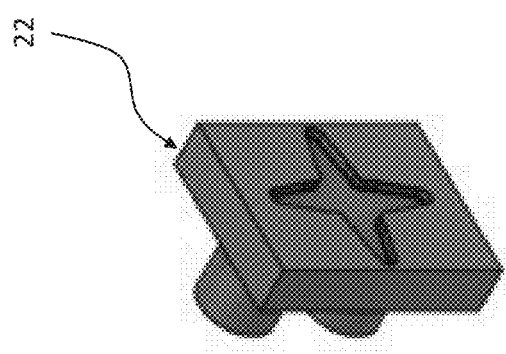
FIG. 10B is a rear perspective view of the plurality of printing platforms of FIG. 10A.
Figure 10A:
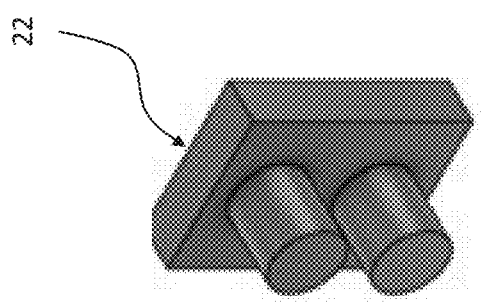
FIG. 10A is a front perspective view of a portion of a plurality of printing platforms of a build platform adaptor that forms a part of a multi-component adaptor assembly, in accordance with an embodiment of the present invention.
Figure 11B:
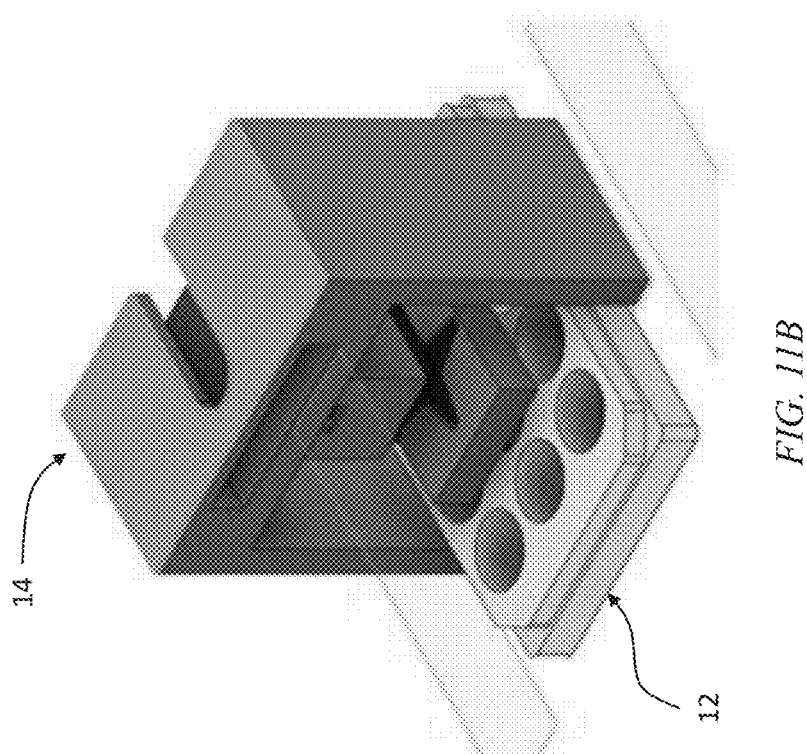
FIG. 11B is a perspective view of the multi-component adaptor assembly of FIGS. 7 and 9-11A, in accordance with an embodiment of the present invention.
Figure 11A:
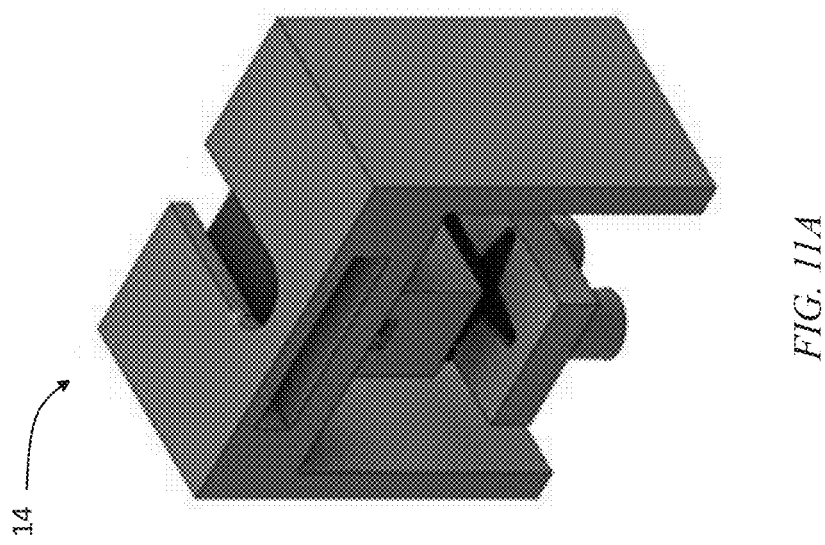
FIG. 11A is a perspective view of an assembled build platform adaptor including the components as shown in FIGS. 10A-10C.

It should be appreciated that the multi-component adaptor assembly can be used in combination with different additive manufacturing devices 10. For example, in an embodiment of the multi-component adaptor assembly as shown in FIGS. 7-9, resin reservoir adaptor 12 includes a plurality of cavities 16 disposed therein that form wells configured to receive an amount of rein therein. In addition, build platform adaptor 14 (shown assembled in FIG. 8D and in component parts in FIGS. 8A-8C) includes a plurality of printing platforms 22 that are sized and shaped to be insertable within each of the plurality of cavities 16 of resin reservoir adaptor 12 (as shown in FIG. 9). Similar to build platform adaptor 14 described in detail above, the plurality of printing platforms 22 are rotatable with respect to connector 18 via translation assembly 20. Similarly, as shown in FIGS. 10A-11B, an embodiment of the multi-component adaptor assembly includes two printing platforms 22 that are sized and shaped to be insertable within each of the plurality of cavities 16 of resin reservoir adaptor 12 (as shown in FIG. 11B).

Example—Microneedle Manufacture

Particularly related to pharmaceutical and biomedical applications, traditional additive manufacturing devices fail to adequately and efficiently print usable products due to complications with existing resins. For example, recently, additive manufacturing has overtaken micromolding as a leading technique for the creation of microneedle patches for transdermal pharmaceutical and other therapeutic transfer to a subject through the outer layer of the subject's skin. However, it has proven challenging within the art to create microneedle patches that are dissolvable via additive manufacturing techniques, since traditional resin materials are not only expensive, but also result in sturdy and resilient structures after curing. As such, the resulting microneedle patches fail to dissolve in the presence of water.

Figure 12:
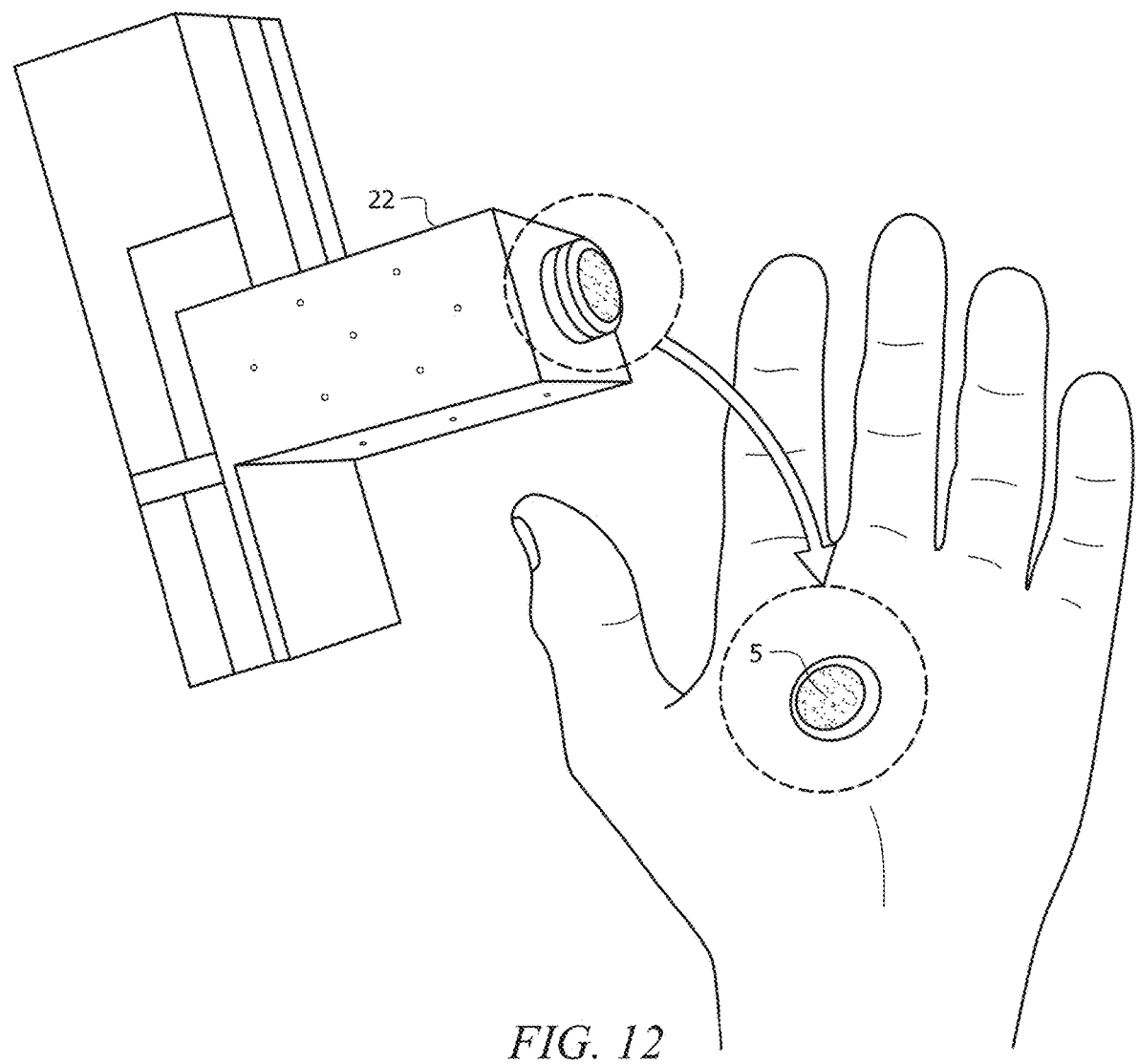
FIG. 12 is a perspective view of an additive manufactured microneedle patch, in accordance with an embodiment of the present invention.

Accordingly, using the multi-component adaptor assembly described above, including resin reservoir adaptor 12 and build platform adaptor 14, a plurality of microneedle patches can be printed during a single printing cycle and using a significantly reduced amount of resin material during the printing cycle. An example of microneedle patch 5 is depicted in FIG. 12. Under the prior art, the manufacture of microneedle patch 5 would typically involve disposing approximately 125 mL of resin within preexisting reservoir 11 and using a single printing platform to create both a backing portion and an applicator portion of microneedle patch 5. Typically, such a printing project would require two cycles—one to create the backing portion, and another to create the applicator portion, due to the differences in resin requirements (i.e., the application portion may require an impregnated therapeutic that would not be required in the backing portion). Alternatively, a single cycle can be used, resulting in the backing portion being impregnated with the therapeutic as well, leading to printing inefficiencies and higher associated costs.

Instead, using the multi-component adaptor assembly, microneedle patch 5 is generated by an additive manufacturing device during a single printing cycle and using approximately 10 mL of resin. The reduced volume of resin is accomplished by the use of resin reservoir adaptor 12 to reduce a volume of resin as compared with preexisting reservoir 11, forming a targeting printing area within the larger preexisting reservoir 11 platform. In addition, the single printing cycle is accomplished via build platform adaptor 14 having a plurality of printing platforms 22 that contact individual ones of a plurality of resin reservoirs of resin reservoir adaptor 12. As such, one reservoir includes an amount of resin without a therapeutic, used to print a blank backing layer of microneedle patch 5; next, build platform adaptor 14 rotates, such that the blank backing layer of microneedle patch 5 subsequently contacts a resin including the therapeutic within a different reservoir of resin reservoir adaptor 12. As such, a plurality of microneedle patches 5 can be printed via the additive manufacturing machine during a single printing cycle, such that each microneedle patch 5 includes a blank backing layer and a therapeutic-impregnated applicator portion, due to the multi-component adaptor assembly.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A multi-component adaptor assembly configured to be in mechanical communication with a translatable printing arm disposed above a printing surface of an additive manufacturing device, the multi-component adaptor assembly comprising:
 a resin reservoir adaptor comprising a plurality of reservoirs, each having an associated area, an associated volume, or both less than an associated area, an associated volume, or both of each printing surface, respectively, the plurality of reservoirs comprising:
  a plurality of interior walls including a set of opposing longitudinal walls each having substantially equal dimensions, and a set of opposing lateral walls each having substantially equal dimensions; and
  a cavity defined by the plurality of interior walls, such that the cavity is defined by a width equal to a distance between the opposing longitudinal walls, and such that the cavity is defined by a length equal to a distance between the opposing lateral walls;
 a build platform adaptor comprising a connector configured to be received by the translatable printing arm of the additive manufacturing device, a plurality of printing platforms, or both, wherein each of the plurality of printing platforms comprises an associated length that is less than the length defining the cavity of the resin reservoir adaptor and includes an associated width that is less than the width defining the cavity of the resin reservoir adaptor;
 wherein at least one portion of the build platform adaptor is configured to rotate about a central point;
 wherein the printing platform is configured to be received within the resin reservoir adaptor via insertion into the cavity;
 wherein the resin reservoir adaptor is configured to store an amount of resin therein within the cavity; and
 wherein at least one of the plurality of printing platforms is configured to print an additive manufactured structure via at least a portion of the amount of resin stored within the cavity, such that a reduced amount of resin is used to print the additive manufactured structure.

2. The multi-component adaptor assembly of claim 1, wherein the resin reservoir adaptor includes a transparent bottom surface wall that defines the cavity together with the plurality of interior walls, the transparent bottom surface wall being configured to allow ultraviolet light to pass therethrough to cure the additive manufactured structure.

3. The multi-component adaptor assembly of claim 1, wherein the distance between the opposing longitudinal walls is 3 cm and the distance between the opposing lateral walls is 6 cm, such that the cavity is configured to receive a volume of the resin equaling 10 mL.

4. The multi-component adaptor assembly of claim 3, wherein the length of the printing platform is 2 cm and the width of the printing platform is 2 cm, such that the printing platform is receivable within the resin reservoir adaptor via the cavity.

5. The multi-component adaptor assembly of claim 1, wherein the resin reservoir adaptor further comprises a plurality of interconnected reservoirs having equal area, volume, or both, whereby at least one of the plurality of interconnected reservoirs comprises a cumulative area, a cumulative volume, or both, that is less than the associated area, the associated volume, or both, of the printing surface, respectively.

6. The multi-component adaptor assembly of claim 5, wherein each of the plurality of interconnected reservoirs includes an identical resin, such that a plurality of identical additive manufactured structures can be printed during a single printing cycle.

7. The multi-component adaptor assembly of claim 5, wherein at least one of the plurality of interconnected reservoirs includes a first resin, and at least one alternative reservoir of the plurality of interconnected reservoirs includes a second resin, such that the additive manufactured structure includes a component made from the first resin and a component made from the second resin.

8. The multi-component adaptor assembly of claim 5, wherein each of the plurality of printing platforms comprise an equal area, an equal volume, or both.

9. The multi-component adaptor assembly of claim 8, wherein at least one of the plurality of printing platforms is simultaneously receivable within at least one of the plurality of interconnected reservoirs.

10. The multi-component adaptor assembly of claim 8, further comprising a translation motor assembly secured at a first end to the connector of the build platform adaptor and secured at an opposing second end to the central point of at least one of the plurality of printing platforms, such that the translation motor assembly is configured to rotate at least one printing platform about the central point.

* * * * *